US012605130B2

(12) United States Patent
Kim et al.

(10) Patent No.: US 12,605,130 B2
(45) Date of Patent: Apr. 21, 2026

(54) RADIOLOGICAL IMAGING EQUIPMENT USING CLIPPING SIGNAL AND SIGNAL PROCESSING DEVICE THEREOF

(71) Applicant: SOGANG UNIVERSITY RESEARCH & BUSINESS DEVELOPMENT FOUNDATION, Seoul (KR)

(72) Inventors: Moo Sub Kim, Jecheon-si (KR); Yong Choi, Seoul (KR); Ji Woong Jung, Seoul (KR)

(73) Assignee: SOGANG UNIVERSITY RESEARCH & BUSINESS DEVELOPMENT FOUNDATION, Seoul (KR)

( * ) Notice: Subject to any disclaimer, the term of this patent is extended or adjusted under 35 U.S.C. 154(b) by 190 days.

(21) Appl. No.: 18/680,459

(22) Filed: May 31, 2024

(65) Prior Publication Data

US 2024/0315652 A1      Sep. 26, 2024

Related U.S. Application Data

(63) Continuation of application No. PCT/KR2022/016264, filed on Oct. 24, 2022.

(30) Foreign Application Priority Data

Dec. 13, 2021    (KR) ......................... 10-2021-0177753

(51) Int. Cl.
*A61B 6/00*        (2024.01)

(52) U.S. Cl.
CPC .................................. *A61B 6/4429* (2013.01)

(58) Field of Classification Search
CPC ........... A61B 6/4429; A61B 6/00; A61B 6/42; A61B 6/5205; G01T 1/161; G01T 1/20; G01T 1/20184
See application file for complete search history.

(56) References Cited

U.S. PATENT DOCUMENTS

| | | | | |
|---|---|---|---|---|
| 5,646,408 | A * | 7/1997 | Goldberg | ................ G01T 1/208 |
| | | | | 250/363.09 |
| 6,362,478 | B1 * | 3/2002 | McDaniel | .............. G01T 1/171 |
| | | | | 250/361 R |

(Continued)

FOREIGN PATENT DOCUMENTS

| | | |
|---|---|---|
| JP | 2018-040800 A | 3/2018 |
| JP | 6863922 B2 | 4/2021 |

(Continued)

OTHER PUBLICATIONS

International Search Report of PCT/KR2022/016264 dated Jan. 27, 2023.

*Primary Examiner* — Kiho Kim
(74) *Attorney, Agent, or Firm* — Bridgeway IP Law Group, PLLC; Jihun Kim

(57) ABSTRACT

Radiological imaging equipment includes a signal detector configured to convert a scintillation signal output from a scintillation crystal into an electrical signal, and a signal processor configured to amplify an output signal of the signal detector and to output a time in which an amplified signal is maintained above a threshold, wherein the signal processor includes a first clipping circuit and a second clipping circuit configured to sequentially clip the amplified signal according to the threshold.

6 Claims, 7 Drawing Sheets

(56)                    References Cited

U.S. PATENT DOCUMENTS

| | | | |
|---|---|---|---|
| 7,504,636 | B1 | 3/2009 | Baxter |
| 8,258,480 | B2 | 9/2012 | Olcott et al. |
| 2018/0113221 | A1* | 4/2018 | Ishikawa ................ C09K 11/02 |

FOREIGN PATENT DOCUMENTS

| | | | |
|---|---|---|---|
| KR | 10-1646651 | B1 | 8/2016 |
| KR | 10-1647395 | B1 | 8/2016 |
| KR | 10-1745436 | B1 | 6/2017 |
| KR | 10-2063828 | B1 | 1/2020 |

* cited by examiner

RADIOLOGICAL IMAGING EQUIPMENT USING CLIPPING SIGNAL AND SIGNAL PROCESSING DEVICE THEREOF

CROSS-REFERENCE TO RELATED APPLICATION

This application is a by-pass continuation of International Application No. PCT/KR2022/016264, filed on Oct. 24, 2022 in the Korean Intellectual Property Receiving Office, which is based on and claims priority to Korean Application No. 10-2021-0177753, filed on Dec. 13, 2021 in the Korean Intellectual Property Office, the entire disclosures of which are incorporated herein by reference.

BACKGROUND

The present disclosure relates to radiological imaging equipment using a clipping signal and a signal processing device of the radiological imaging equipment.

Among various types of radiological medical imaging equipment that have been widely used recently, a scintillation method detects radiation rays and converts the radiation rays into an optical signal, and obtains an image signal of an object by using the converted optical signal. In this case, a multi-channel radiation detector is used to provide accurate anatomical/physiological image information. For example, radiological imaging equipment, such as an X-ray apparatus, a computed tomography (CT), a positron emission tomography (PET), or a gamma camera uses optical sensors with a large number of channels per unit area to improve performance. Due to an increase in channels, a signal processing burden increases when acquiring and processing data.

In addition, various methods are being studied to more accurately distinguish the energy of radiation detected by radiological imaging equipment. A mainly-used data acquisition system uses a method of analyzing the energy and time information of radiation by using an analog-to-digital convertor (ADC) or a time-to-digital convertor (TDC). Because the increase in channels and the method of analyzing data increase the complexity of a data acquisition system, research is continuously being conducted to minimize complexity by reducing input data or simplifying the data acquisition system.

Time over threshold (TOT) signal processing uses a method of analyzing energy and time information by using a width of a detected radiation signal, and may configure a data acquisition system with only a TDC without using an ADC, and accordingly, there is an advantage in that complexity may be reduced. However, the data acquisition system using a TOT-TDC has poor energy linearity, and thus, the data acquisition system may not be applied to X-rays with continuous energy and gamma-rays with a close optical peak.

In order to solve the problems, the present disclosure provides a signal processing device that may increase energy linearity while maintaining complexity reduction, which is an advantage of the TOT-TDC structure, by using a diode-based clipping circuit.

SUMMARY

The present disclosure provides a signal processing device that may increase energy linearity by using a diode-based clipping circuit, and radiological imaging equipment using the signal processing device.

Problems to be solved by the present embodiment are not limited to the problem described above, and there may be other problems.

According to an aspect of the present disclosure, radiological imaging equipment includes a signal detector configured to convert a scintillation signal output from a scintillation crystal into an electrical signal, and a signal processor configured to amplify an output signal of the signal detector and to output a time in which an amplified signal is maintained above a threshold, wherein the signal processor includes a first clipping circuit and a second clipping circuit configured to sequentially clip the amplified signal according to the threshold.

According to another aspect of the present disclosure, a signal processing device for radiological imaging equipment includes an amplifier configured to amplify an input signal obtained by converting a scintillation signal into an electrical signal, a first clipping circuit and a second clipping circuit configured to sequentially clip an output signal of the amplifier according to a threshold, and a time-to-digital convertor configured to measure an output signal of the second clipping circuit.

BRIEF DESCRIPTION OF THE DRAWINGS

Embodiments of the inventive concept will be more clearly understood from the following detailed description taken in conjunction with the accompanying drawings in which.

DETAILED DESCRIPTION OF THE EMBODIMENTS

Figures 1, 2:
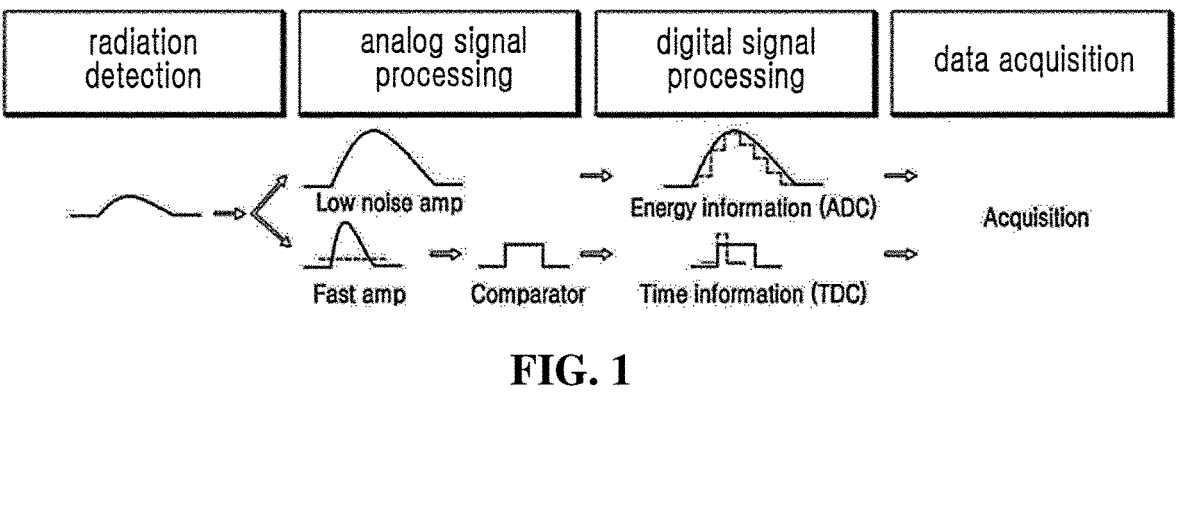
FIGS. 1 and 2 illustrate signal processing of general radiological imaging equipment.

Hereinafter, embodiments of the present disclosure will be described in detail with reference to the accompanying drawings such that those skilled in the art in which the present disclosure belongs may easily practice the present disclosure. However, the present disclosure may be implemented in many different forms and is not limited to the embodiments described herein. In addition, in order to clearly describe the present disclosure, parts irrelevant to the description are omitted in the drawings, and similar reference numerals are attached to similar parts throughout the specification.

When it is described that a portion is "connected" to another portion throughout the specification, this includes not only a case where the portion is "directly connected" to another portion but also a case where the portion is "electrically connected" to another portion with another component therebetween.

When it is described that a member is "on" another member throughout the specification, this includes not only a case where a member is in contact with another member, but also a case where there is another member between the two members.

Throughout the present disclosure, when a portion "includes (comprises or provides)" a certain component, this does not exclude other components, and means to "include (comprise or provide)" other components unless otherwise described. Terms "about", "substantially", and so on, which are used throughout the specification, are used to mean a value or another value close to the value when manufacturing and material tolerances inherent to the stated meaning are given, and are used to prevent unscrupulous infringers from taking unfair advantage of disclosures that state precise or absolute figures to aid understanding of the disclosure. Term "step" or "step of", which is used throughout the specification, does not mean "step for".

Hereinafter, embodiments of the present disclosure will be described in detail with reference to the attached drawings.

Figure 3:
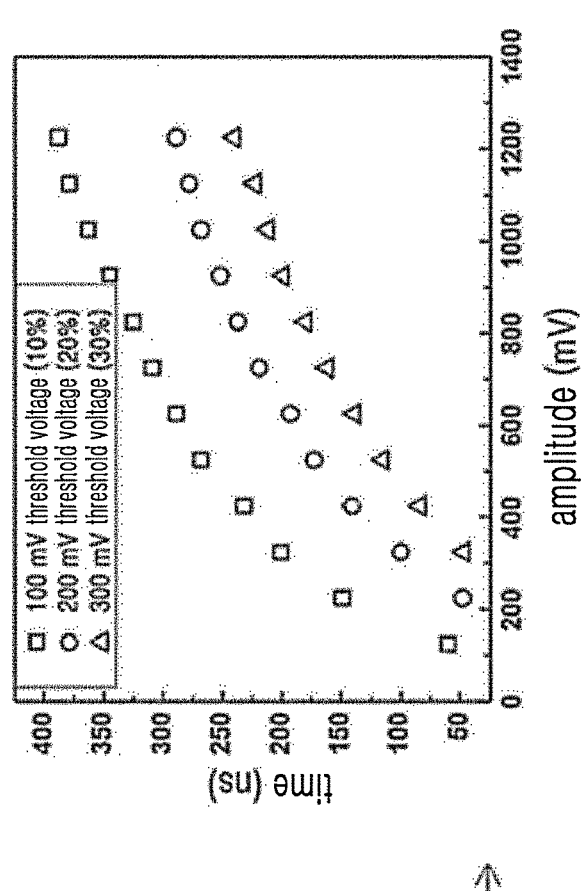
FIG. 3 is a diagram illustrating non-linearity which is a disadvantage of the conventional technology.
Figure 3:
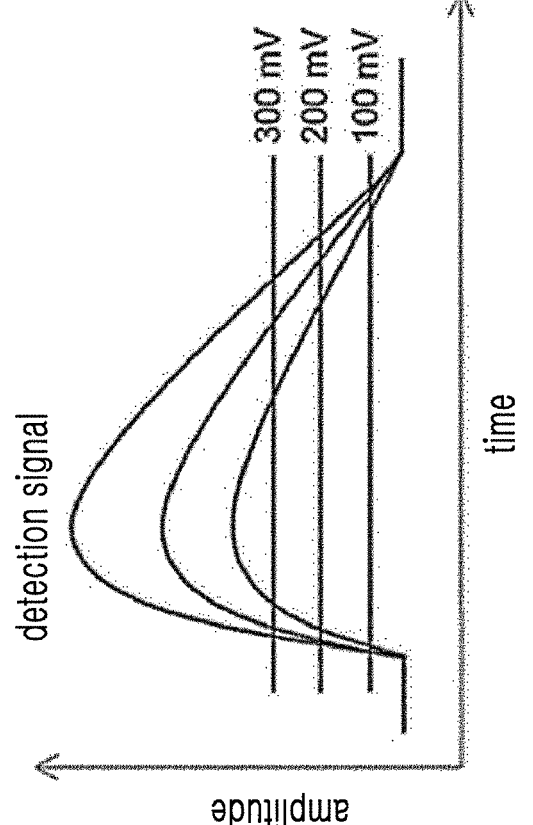

FIGS. 1 and 2 illustrate signal processing of a general radiological imaging equipment, and FIG. 3 is a diagram illustrating shortcomings of the conventional technology.

As illustrated in the drawings, data is obtained through a radiation detection process, analog signal processing for the radiation detection process, and digital conversion processing of an analog signal.

As illustrated in FIG. 1, an analog-to-digital conversion method or a time-to-digital conversion method are known as a method of analyzing energy and time information on a detected radiation signal, In particular, FIG. 2 describes a time-to-digital conversion process in detail.

Unlike the analog-to-digital conversion method, the time-to-digital conversion method is a method of acquiring only the time information on maintaining a signal above a threshold as a digital signal, and has an advantage in that the method is simple.

However, as illustrated in FIG. 3, there is a disadvantage in that linearity is reduced compared to the analog-to-digital conversion method. That is, the analog-to-digital conversion method uses the amplitude of a signal to maintain linearity, while the time-to-digital method acquires only information on the time in which a signal is maintained, and accordingly, so the time-to-digital method is non-linear compared to the analog-to-digital conversion method. This is because the rising time and falling time of an output signal of a scintillation detector used by radiological medical imaging equipment are different from each other, and the falling time is relatively slow. This is due to the physical characteristics of a scintillator and the quenching characteristics of an optical sensor, which results in nonlinearity in signal amplitude versus width.

Figure 4:
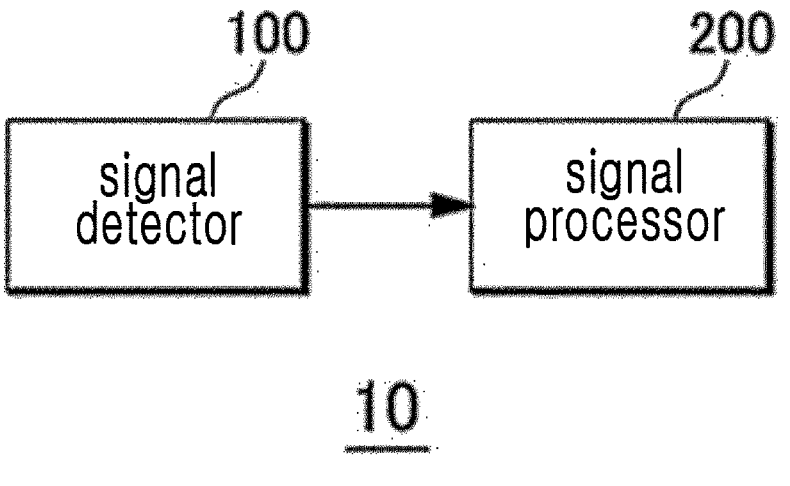
FIG. 4 is a block diagram illustrating a configuration of radiological imaging equipment according to an embodiment of the present disclosure.

FIG. 4 is a block diagram illustrating a configuration of a radiological imaging equipment 10 according to an embodiment of the present disclosure.

The radiological imaging equipment 10 includes a signal detector 100 that converts a scintillation signal output from scintillation crystal into an electrical signal, and a signal processor 200 that amplifies an output of the signal detector 100 and outputs the time in which an amplified signal is maintained above a threshold.

The radiological imaging equipment 10 to which the present disclosure is applied includes X-ray, dual-energy x-ray absorptiometry (DEXA), computed tomography (CT), single photon emitted computed tomography (SPECT), positron emission tomography (PET), or a gamma camera.

also, the signal detector 100 detects radiation rays emitted from Radiopharmaceuticals injected into an object or radiation rays emitted to and transmitted through the object, and generates a radiation detection signal indicating the distribution of the body or organs. To this end, the signal detector 100 may include a plurality of scintillation crystals that convert radiation rays into scintillation signals, and a plurality of optical sensors that convert a scintillation signal output from the scintillation crystal into an electrical signal.

The scintillation crystal be bismuth germanate oxide (BGO), lutetium oxyorthosilicate (LSO), lutetium yttriumoxyorthosilicate (LYSO), lutetium aluminum perovskite (LuAP), lutetium yttrium aluminum perovskite (LuYAP), lanthanum bromide (LaBr3), lutetium Iodide (LuI3), gadolinium oxyorthosilicate (GSO), lutetium gadolinium oxyorthosilicate (LGSO), lutetium aluminum garnet (LuAG), gadolinium gallium garnet (GAGG), or so on, but is not limited thereto. In addition, the optical sensor may include silicon photo multiplier (SiPM), multi-pixel photon counter (MPPC), CdZnTe (CZT), CdTe, avalanche photo diode (APD), a PIN diode, and a digital silicon photomultiplier (dSiPM), a multi-channel photomultiplier tube, or so on. In this case, the radiation rays detected by the optical sensor may include not only gamma rays, but also X-rays, alpha rays, beta rays, neutron rays, and so on, and the present disclosure may be applied to other electromagnetic waves in addition to the radiation rays.

The signal processor 200 includes an analog circuit that amplifies and clips a signal, and a time-to-digital convertor (TDC) that converts an output signal of the analog circuit into a digital signal.

Also, the signal processor 200 includes a first clipping circuit and a second clipping circuit that sequentially clip an amplified signal according to a threshold.

Figure 5:
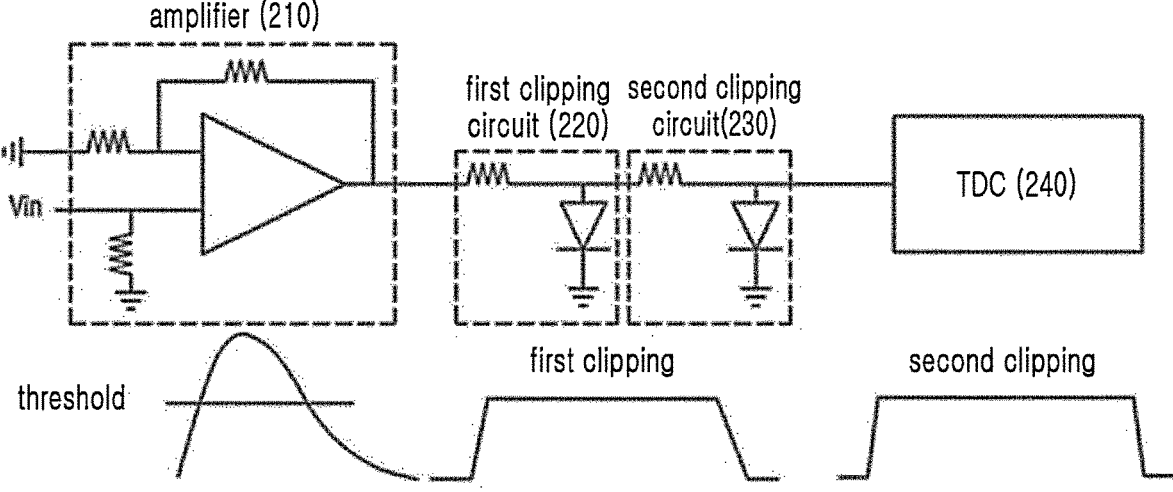
FIG. 5 is a circuit diagram specifically illustrating a configuration of a signal processing unit according to an embodiment of the present disclosure.

FIG. 5 is a circuit diagram specifically illustrating a configuration of a signal processor, according to an embodiment of the present disclosure.

The signal processor 200 includes an amplifier 210 that amplifies an output signal of the signal detector 100, a first clipping circuit 220 including a first diode connected between an output terminal of the amplifier 210 and the ground, a second clipping circuit 230 including a second diode connected between an output terminal of the first clipping circuit 220 and the ground, and a TDC 240 that measures an output of the second clipping circuit 230.

The amplifier 210 may include an operational amplifier and so on, and an appropriate resistor may be additionally connected thereto to adjust an amplification ratio. Since a configuration of the amplifier 210 uses a well-known technology, detailed description there is omitted.

The first clipping circuit 220 removes a signal exceeding a threshold voltage among the signals output from the output terminal of the amplifier 210 through the ground, and transmits the other clipped signals to the second clipping circuit 230. Accordingly, the time in which a signal exceeding the threshold voltage is maintained may be detected. In this case, a forward voltage of a diode included in the first clipping circuit 220 may be used as the threshold voltage, for example, 0.7 V.

The second clipping circuit 230 removes a signal exceeding the threshold voltage among the signals output from an output terminal of the first clipping circuit 220 and transmits the other clipped signals to the TDC 240.

In this way, two clipping operations are performed continuously on a detection signal, and it can be seen that rising time and falling time of a clipping signal output from the second clipping circuit 230 are steeper than rising time and falling time of an output signal of the first clipping circuit 220.

This is due to reverse recovery time characteristics of diodes included in the first and second clipping circuits 220 and 230), and is also because, even when a voltage of an output signal of the amplifier 210 exceeding a threshold voltage of the diode is lower than the threshold voltage of the diode, the diode maintains a forward voltage for a certain period of time. During the certain period of time, the diode is turned on, and thereby, a current flows therethrough, and the current due to radiation detection completely flows therethrough before a reverse recovery time ends. More specifically, charge carriers pass through a depletion region to generate a forward current in a diode operating in a forward bias, and it is impossible to immediately stop the flow of the charge carriers even when a bias of the diode is reversed.

Due to this, the larger the size of an output signal of the amplifier 210, the longer the reverse recovery time of diodes of the first and second clipping circuits 220 and 230, and a current-width relationship is formed rather than a signal amplitude-width relationship, which makes a difference between a start point and an end point of a signal to be clearer, and based thereon, a nonlinearity of a time-to-digital technique for analyzing energy information may be increased.

Also, the TDC 240 converts an output signal of the second clipping circuit 230 into a digital signal. In this case, in order to measure the time in which a second clipping signal is maintained, clock pulses are repeatedly applied, and the number of pulses is counted, and accordingly, a retention time of the second clipping signal may be measured.

Figure 6:
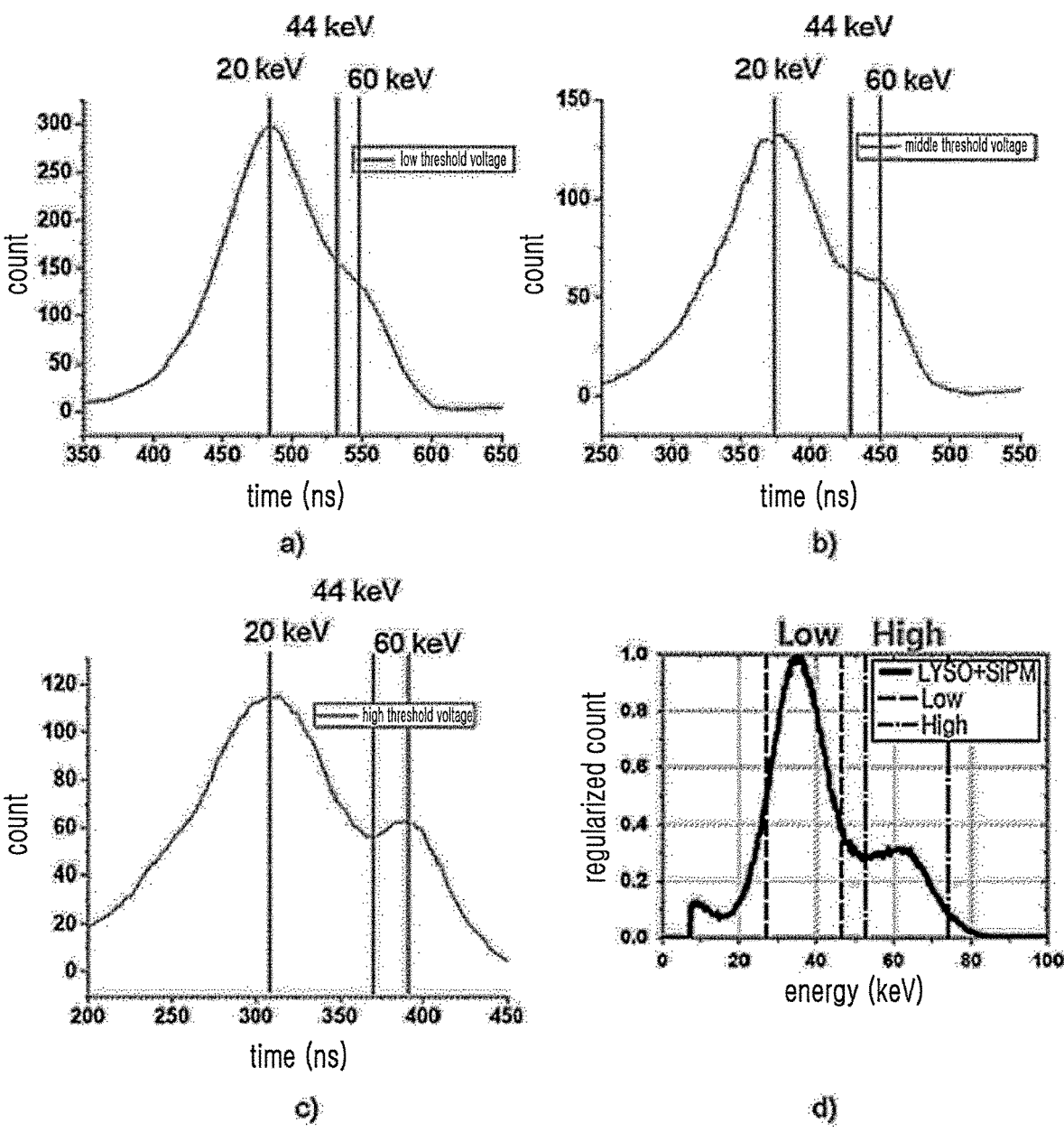
FIGS. 6 and 7 are graphs illustrating effects of a signal processing device according to an embodiment of the present disclosure.
Figure 7:
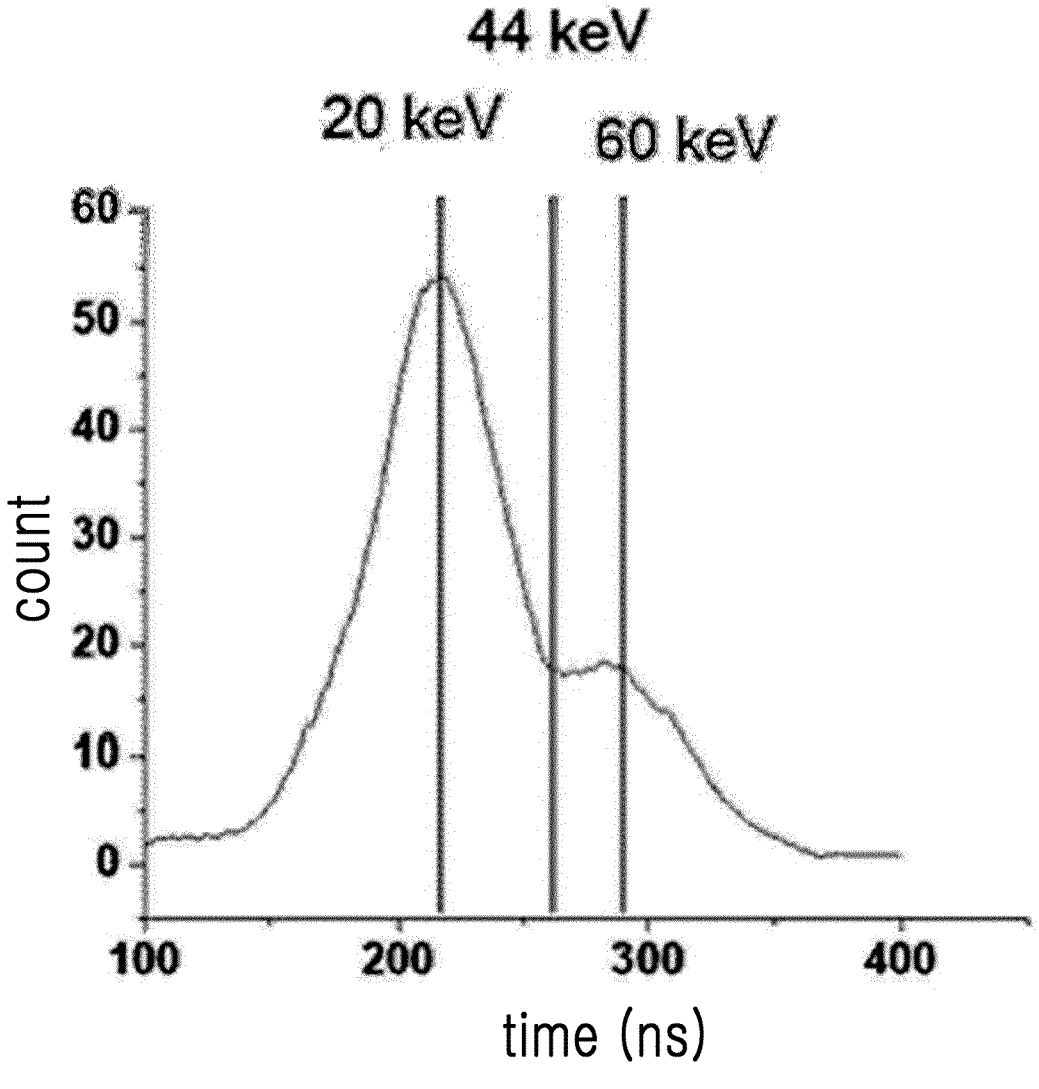

FIGS. 6 and 7 are diagrams illustrating effects of a signal processing device according to an embodiment of the present disclosure.

FIG. 6 illustrates an energy spectrum of X-rays (~83 keV) acquired by using the conventional time over threshold (TOT) signal processing method and a TDC-based data acquisition system. FIG. 6 are graphs illustrating results of measurement by using an X-ray generator of a bone density meter using a samarium filter that blocks a 44 keV energy region, and the spectra of a), b), and c) are results of applying three levels of threshold voltages (a low level, a middle level, and a high level). As illustrated in FIG. 6, when the threshold voltage is in the low level, a detectable region is wide and linearity is reduced, and when the threshold voltage is in the high level, the detectable region is narrow and the linearity is increased, and thereby, a region of 20 keV and a region of 60 keV are well distinguished. However, when compared to a spectrum of d), which is reference data obtained according to an analog-to-digital technique, it can be seen that there are many differences in count distribution and linearity.

FIG. 7 is a graph illustrating an X-ray spectrum acquired by using a clipping circuit according to an embodiment of the present disclosure, and it can be seen that a count distribution is similar to the graph d) of FIG. 6 which is the reference data.

Figure 8:
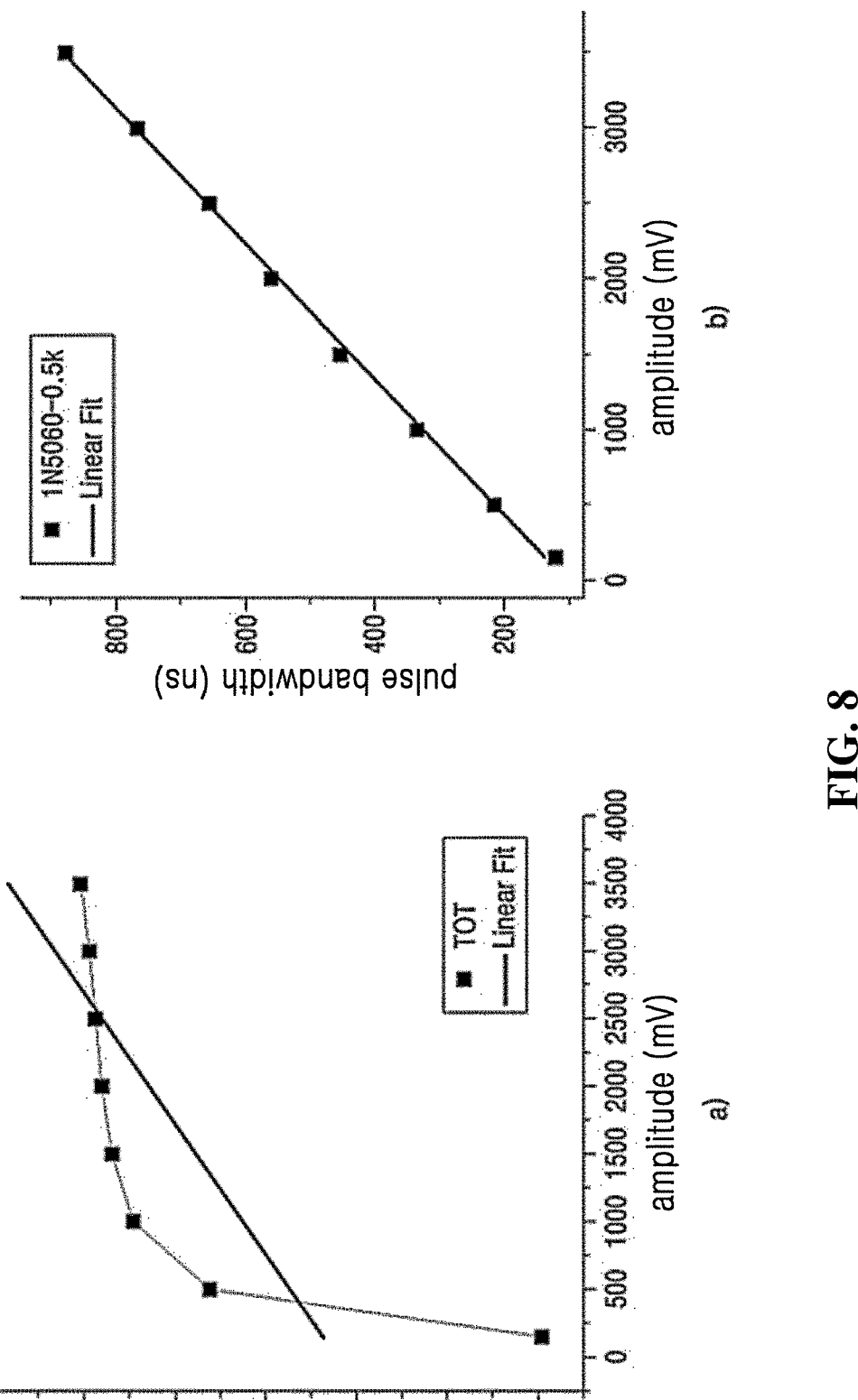
FIG. 8 is a graph illustrating an evaluating linearity of a clipping circuit according to an embodiment of the present disclosure and the conventional TOT method.

In addition, as illustrated in FIG. 8, it can be seen that a clipping circuit according to an embodiment of the present disclosure has improved results than the conventional TOT method in evaluating linearity.

A comparator used for a TOT-TDC data acquisition method in the related art outputs a digital signal at a point where a voltage crosses the set threshold voltage. There is no problem when a ratio of a height and width of an output signal of a scintillation detector used in radiological medical imaging equipment is linear, but the height and width of a signal are not linear. This is because falling time is relatively slow compared to rising time of an output signal.

In order to solve the problem, the present disclosure provides a linear effect by analyzing a signal in terms of a relationship between a current and a width because, when a signal above a threshold voltage is input, a clipping signal begins to rise (a rising edge), and when a diode's recovery time and a current's flow end, the clipping signal ends (a falling edge).

According to the present disclosure, low energy linearity may be increased which is a drawback of radiation measurement and imaging equipment including TOT signal processing and TDC-based data acquisition system, and thus, accuracy and resolution may be increased, and image resolution may be increased. Also, unlike gamma rays with photonic crystals, continuous X-rays have low energy linearity and difficulty in accurate measurement, but the present disclosure may be more effective in X-rays with a low energy region and a continuous spectrum.

In addition, embodiments of the present disclosure may also be implemented in the form of a recording medium including instructions executable by a computer, such as a program module executed by the computer. A computer readable medium may be any available medium that may be accessed by a computer and includes both volatile and nonvolatile media, removable and non-removable media. Also, the computer readable medium may include a computer storage medium. A computer storage medium includes both volatile and nonvolatile media and removable and non-removable media implemented by any method or technology for storing information, such as computer readable instructions, data structures, program modules or other data.

Although the method and system of the present disclosure are described with respect to specific embodiments, some or all of components or operations thereof may be implemented by using a computer system having a general-purpose hardware architecture.

The above descriptions of the present disclosure are for illustrative purposes only, and those skilled in the art to which the present disclosure belongs will understand that the present disclosure may be easily modified into another specific form without changing the technical idea or essential features of the present disclosure. Therefore, the embodiments described above should be understood as illustrative in all respects and not limiting. For example, each component described as a single type may be implemented in a distributed manner, and similarly, components described in a distributed manner may also be implemented in a combined form.

The scope of the present disclosure is indicated by the following claims rather than the detailed description above, and the meaning and scope of the claims and all changes or modifications derived from the equivalent concepts should be interpreted as being included in the scope of the present disclosure.

What is claimed is:

1. Radiological imaging equipment comprising:
   a signal detector configured to convert a scintillation signal output from a scintillation crystal into an electrical signal; and
   a signal processor configured to amplify an output signal of the signal detector and to output a time in which an amplified signal is maintained above a threshold, wherein the signal processor includes a first clipping circuit and a second clipping circuit configured to sequentially clip the amplified signal according to the threshold.

2. The radiological imaging equipment of claim 1, wherein the signal processor includes:

an amplifier configured to amplify the output signal of the signal detector;

a first clipping circuit including a first diode connected between an output terminal of the amplifier and a ground;

a second clipping circuit including a second diode connected between an output terminal of the first clipping circuit and the ground; and a time-to-digital convertor configured to measure an output signal of the second clipping circuit.

3. The radiological imaging equipment of claim 1, wherein a rising edge and a falling edge of the output signal of the second clipping circuit are steeper than a rising edge and a falling edge of an output signal of the first clipping circuit.

4. A signal processing device for radiological imaging equipment, the signal processing device comprising:

an amplifier configured to amplify an input signal obtained by converting a scintillation signal into an electrical signal;

a first clipping circuit and a second clipping circuit configured to sequentially clip an output signal of the amplifier according to a threshold; and a time-to-digital convertor configured to measure an output signal of the second clipping circuit.

5. The signal processing device of claim 4, wherein the first clipping circuit includes a first diode connected between an output terminal of the amplifier and a ground, and the second clipping circuit includes a second diode connected between an output terminal of the first clipping circuit and the ground.

6. The signal processing device of 4, wherein a rising edge and a falling edge of the output signal of the second clipping circuit are steeper than a rising edge and a falling edge of an output signal of the first clipping circuit.

* * * * *